United States Patent [19]

Kawamoto et al.

[11] Patent Number: 5,068,377

[45] Date of Patent: Nov. 26, 1991

[54] BETAINE-CONTAINING SILOXANE COMPOUNDS AND METHOD FOR MAKING

[75] Inventors: Hideyuki Kawamoto; Shoji Ichinohe, both of Annaka; Kazuyuki Tsubone, Hiratsuka, all of Japan

[73] Assignee: Shin-Etsu Chemical Co., Ltd., Tokyo, Japan

[21] Appl. No.: 598,434

[22] Filed: Oct. 16, 1990

[30] Foreign Application Priority Data

Oct. 16, 1989 [JP] Japan .................................. 1-269897

[51] Int. Cl.$^5$ .............................................. C07F 7/10
[52] U.S. Cl. ................................................. 556/418
[58] Field of Search ....................................... 586/418

[56] References Cited

U.S. PATENT DOCUMENTS

| 4,342,742 | 8/1982 | Sebug et al. | 556/418 X |
| 4,511,727 | 4/1985 | Martin | 556/418 |
| 4,912,240 | 3/1990 | Owen et al. | 556/418 |

FOREIGN PATENT DOCUMENTS 0295593  12/1988  Japan .................................. 556/418

Primary Examiner—Paul F. Shaver
Attorney, Agent, or Firm—Birch, Stewart, Kolasch & Birch

[57] ABSTRACT

Siloxane compounds having a hydroxyalkyl radical incorporated in their betaine moiety exhibit improved surface tension reduction and are thus useful hair cleaning agents. They can be efficiently synthesized at a low cost without autoclaving.

18 Claims, No Drawings

BETAINE-CONTAINING SILOXANE COMPOUNDS AND METHOD FOR MAKING

This invention relates to siloxane compounds containing a betaine radical having a hydroxyalkyl radical incorporated therein for use as surface active agents, hair cleaning agents, and fiber treating agents.

BACKGROUND OF THE INVENTION

Betaine radical-containing siloxane compounds are well known in the art as disclosed in U.S. Pat. Nos. 4,654,161 (Japanese Patent Publication No. 16418/1988), 4,496,705, and 4,609,750, for example. They are widely used as surface active agents in shampoo, conditioners and other hair cleaning compositions.

However, prior art well-known betaine radical containing siloxane compounds are limited in their ability to reduce surface tension. Therefore, there is a need for a siloxane compound which when blended in hair cleaning compositions, can further improve the feel including hair texture and smooth combing.

Synthesis of such prior art betaine radical-containing siloxane compounds involves autoclaving because dimethyl amine having a low boiling point of 7° C. is used. This is not only disadvantageous in mass production because of low yields and increased costs, but also arises a safety problem.

SUMMARY OF THE INVENTION

Therefore, a primary object of the present invention is to provide a betaine radical-containing siloxane compound having improved surface tension reducing ability. Another object of the present invention is to provide a method for preparing a betaine radical-containing siloxane compound without autoclaving.

The inventors have found that the above and other objects can be attained by tailoring a betaine radical containing siloxane compound by introducing a hydroxyalkyl radical into the betaine radical, that is, by substituting a hydroxyalkyl radical for one or both of the two alkyl radicals in the betaine radical.

According to the present invention, there is provided a betaine radical-containing siloxane compound having the following formula:

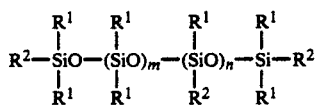

wherein each $R^1$ is independently selected from substituted or unsubstituted monovalent hydrocarbon radicals having 1 to 18 carbon atoms, each $R^2$ is independently selected from the group consisting of a substituted or unsubstituted monovalent hydrocarbon radical having 1 to 18 carbon atoms and a monovalent organic radical of the formula:

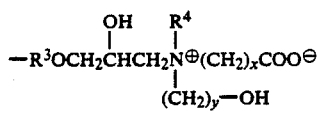

wherein $R^3$ is a divalent hydrocarbon radical having 1 to 10 carbon atoms, $R^4$ is an alkyl radical having 1 to 3 carbon atoms or $-(CH_2)_y-OH$, letters x and y are integers of from 1 to 3, with the proviso that at least one of $R^2$ substituents is of formula (2), and letters m and n are integers of from 0 to 1000.

The present invention also provides a method for such a betaine radical-containing siloxane compound, comprising the steps of:

reacting a compound of the formula:

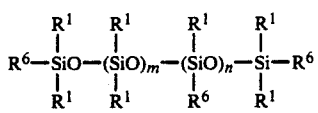

wherein each $R^1$ is independently selected from substituted or unsubstituted monovalent hydrocarbon radicals having 1 to 18 carbon atoms, each $R^6$ is an organic radical independently selected from the group consisting of a substituted or unsubstituted monovalent hydrocarbon radical having 1 to 18 carbon atoms and a monovalent organic radical of the formula:

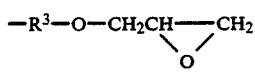

wherein $R^3$ is a divalent hydrocarbon radical having 1 to 10 carbon atoms, with the proviso that at least one of $R^6$ substituents is of formula (4), and letters m and n are integers of 0 to 1000, with an N-alkylaminoalcohol of the following formula:

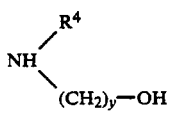

wherein $R^4$ is an alkyl radical having 1 to 3 carbon atoms and y is an integer of 1 to 3, under atmospheric pressure, thereby causing cleavage of the epoxy radical in the organic radical of formula (4) to convert the organic radical into an organic radical of the following formula:

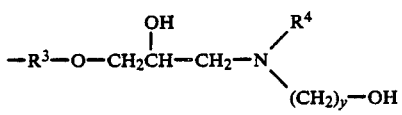

wherein $R^3$, $R^4$, and y are as defined above, thus synthesizing a siloxane compound having the organic radical of formula (6), and reacting said compound with a compound of the following formula:

wherein X is a halogen atom, M is an alkali metal ion, and x is an integer of 1 to 3.

Several benefits of the present invention are discussed below. The betaine radical used in the prior art is typically represented by the following formula.

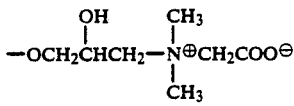

Synthesis of silicone compounds having such a betaine radical involves reaction between a secondary amine in the form of dimethylamine and an epoxy radical-containing siloxane compound. This reaction must be done in an autoclave because dimethylamine has a low boiling point of 7° C. Quite unexpectedly, we have found that reaction of an organic radical of formula (4) with an N-alkylaminoalcohol of formula (5) proceeds efficiently even under atmospheric pressure.

Silicone compounds have to be water soluble in order to act as components of hair cleaning compositions although the more the water-insoluble silicone moiety, the more is reduced the surface tension. Since the siloxane compound of formula (1) in which a hydroxyalkyl radical is incorporated into the betaine radical using the N-alkylaminoalcohol is more water soluble than the conventional hydroxyalkyl-free betaine radical, it is possible to impart water solubility to the silicone by incorporating a hydroxyalkyl radical into the betaine without sacrificing the surface tension by the water-insoluble silicone moiety. Therefore, the siloxane compound having an organic radical of formula (2) is improved in surface tension reduction over the conventional betaine radical-containing siloxane compounds and thus, when blended in hair cleaning compositions, successful in a pleasant feel on use including hair texture and smooth combing.

DETAILED DESCRIPTION OF THE INVENTION

The siloxane compound of the present invention is represented by formula (1).

$$R^2-\underset{\underset{R^1}{|}}{\overset{\overset{R^1}{|}}{Si}}O-(\underset{\underset{R^1}{|}}{\overset{\overset{R^1}{|}}{Si}}O)_m-(\underset{\underset{R^2}{|}}{\overset{\overset{R^1}{|}}{Si}}O)_n-\underset{\underset{R^1}{|}}{\overset{\overset{R^1}{|}}{Si}}-R^2 \quad (1)$$

In formula (1), $R^1$ is independently selected from substituted or unsubstituted monovalent hydrocarbon radicals having 1 to 18 carbon atoms, preferably 1 to 6 carbon atoms, for example, methyl, ethyl, and phenyl radicals.

$R^2$ is independently selected from the group consisting of a substituted or unsubstituted monovalent hydrocarbon radical having 1 to 18 carbon atoms as defined for $R^1$ and a monovalent organic radical of the formula:

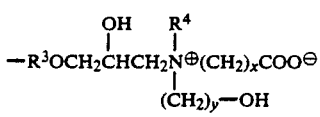

with the proviso that at least one of $R^2$ substituents is of formula (2). In formula (2), $R^3$ is a divalent hydrocarbon radical having 1 to 10 carbon atoms, preferably 1 to 4 carbon atoms, for example, $-(CH_2)_3-$, $-(CH_2)_4-$, and

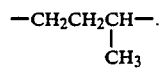

$R^4$ is an alkyl radical having 1 to 3 carbon atoms such as methyl or $-(CH_2)_y-OH$. Letters x and y are integers of from 1 to 3, preferably y being equal to 2.

In formula (1), letter m is an integer of from 0 to 1000, preferably 4 to 10, and letter n is an integer of from 0 to 1000, preferably 0 to 5.

Examples of the siloxane compound having formula (1) are given below.

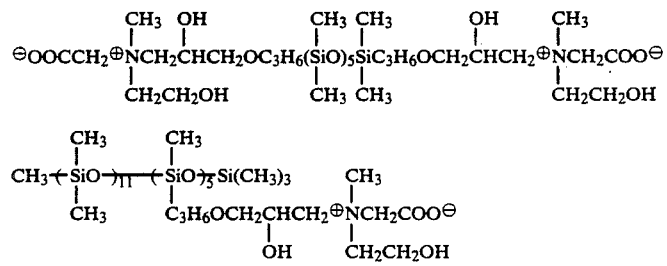

The siloxane compound of formula (1) is prepared by a compound of the formula:

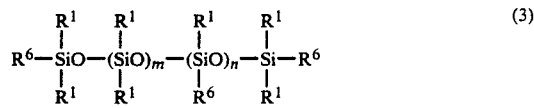

wherein $R^1$, m and n are as defined above, $R^6$ is the same as $R^1$ or a monovalent organic radical of the formula:

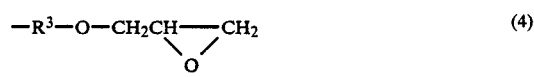

wherein $R^3$ is as defined above, with the proviso that at least one of $R^6$ substituents is of formula (4), with an N-alkylaminoalcohol of the following formula:

wherein $R^4$ and y are as defined above, thereby opening the epoxy ring in the organic radical of formula (4) to convert the organic radical of formula (4) into an organic radical of the following formula:

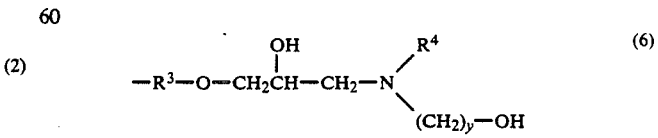

wherein $R^3$, $R^4$, and y are as defined above, thus synthesizing a siloxane compound having the organic radical of formula (6). This reaction is designated Reaction I.

Next, the compound resulting from Reaction I is reacted with a compound of the following formula:

$$X-(CH_2)_x-COO^\ominus M^\oplus \quad \ldots (7)$$

wherein X is a halogen atom such as chloro or bromo, M is an alkali metal ion such as sodium and potassium cations, and x is as defined above in an aqueous system, an aqueous lower alcohol system (e.g., methanol, ethanol, and isopropanol) or an aqueous polyhydric alcohol system (e.g., glycerine, ethylene glycol, and propylene glycol). This reaction is designated Reaction II. As a result, there is obtained a betaine radical-containing siloxane compound of formula (1).

In Reaction I, examples of the N-alkylaminoalcohol formula (5) include N-methylaminoethanol and diethanolamine. The use of N-alkylaminoalcohol as the secondary amine rather than the conventional dimethylamine allows Reaction I to proceed under atmospheric pressure. The reaction temperature preferably ranges from 50° to 150° C., especially from 80° to 100° C., and the reaction time generally ranges from 4 to 6 hours.

In Reaction II, the reaction temperature preferably ranges from 80° to 150° C., especially from 90° to 110° C., and the reaction time generally ranges from 12 to 16 hours. Reaction II can also be effected under atmospheric pressure.

The compounds of formula (1) can be prepared by reacting a compound having the following formula:

$$\begin{array}{c} R^1 \quad R^1 \quad R^1 \quad R^1 \\ | \quad | \quad | \quad | \\ R-SiO-(SiO)_m-(SiO)_n-Si-R \\ | \quad | \quad | \quad | \\ R^1 \quad R^1 \quad R \quad R^1 \end{array}$$

wherein R is of formula (6) and $R^1$ is as defined above with a compound having the following formula:

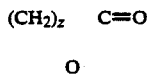

wherein z ranges from 2 to 5. Preferred reaction conditions include a temperature of 25° to 110° C., especially 25° to 80° C., a time of 3 to 12 hours, and an atmospheric pressure. Solvents such as acetonitrile, diethyl ether, isopropyl alcohol, and propylene glycol are preferably used.

The siloxane compounds according to the present invention have improved surface tension reducing ability over the conventional betaine radical-containing siloxane compounds. When blended in hair cleaning compositions, typically shampoo and conditioners, they are successful in imparting a pleasant feel on use including hair texture and smooth combing. They are also useful as fiber treating agents.

There have been described siloxane compounds of formula (1) which, owing to inclusion of an organic radical having a hydroxyalkyl radical incorporated in its betaine moiety, exhibit surface tension reducing ability at least equivalent to the conventional betaine radical-containing siloxane compounds. These siloxane compounds can be synthesized in high yields at a low cost without autoclaving.

EXAMPLE

In order that those skilled in the art better understand the present invention, examples of the invention are given below by way of illustration and not by way of limitation.

EXAMPLE 1

A 1-liter flask equipped with a thermometer, stirrer, and reflux condenser was charged with 500 grams (0.76 mol) of a siloxane compound having the following average composition formula:

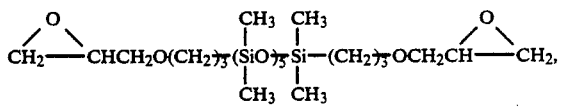

114 grams (1.52 mol) of N-methylaminoethanol, and 100 grams of isopropanol. The contents were allowed to react for 4 hours under reflux conditions. From this reaction solution, a low-boiling fraction was vacuum distilled off at 80° C./4 mmHg over 4 hours. The resulting reaction product or siloxane compound had a viscosity of 327 centistokes at 25° C., a specific gravity of 1.010, an index of refraction of 1.4455, and an amine equivalent of 414 grams/mol.

Next, a 1-liter flask was charged with 200 grams (0.25 mol) of the siloxane compound prepared above, 57 grams (0.49 mol) of sodium monochloroacetate in 134 grams of water, and 173 grams of 1,2-propylene glycol. With stirring, the contents were allowed to react at 100° C. for 15 hours. There was obtained a water/propylene glycol solution of a siloxane compound having the following average composition formula.

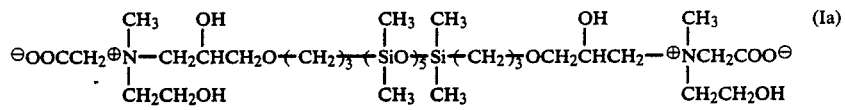

For surface tension measurement, a 0.1 wt % aqueous solution was prepared from the siloxane compound having average composition formula (Ia). The surface tension was 26.5 dyne/cm at 20° C.

EXAMPLE 2

A 1-liter flask equipped with a thermometer, stirrer, and reflux condenser was charged with 400 grams (0.23 mol) of a siloxane compound having the following average composition formula:

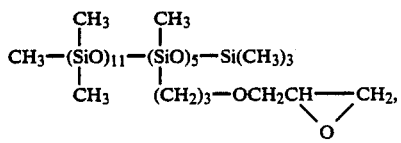

169 grams (2.25 mol) of N-methylaminoethanol, and 200 grams of isopropanol. The contents were allowed to react for 6 hours under reflux conditions. From this reaction solution, a low-boiling fraction was vacuum distilled off at 80° C./4 mmHg over 4 hours. The resulting reaction product or siloxane compound had a viscosity of 2932 centistokes at 25° C., a specific gravity of 1.044, an index of refraction of 1.4493, and an amine equivalent of 392 grams/mol.

Next, a 1-liter flask was charged with 200 grams (0.09 mol) of the siloxane compound prepared above, 54 grams (0.46 mol) of sodium monochloroacetate in 130 grams of water, and 186 grams of 1,2-propylene glycol. With stirring, the contents were allowed to react at 100° C. for 12 hours. There was obtained a water/propylene glycol solution of a siloxane compound having the following average composition formula.

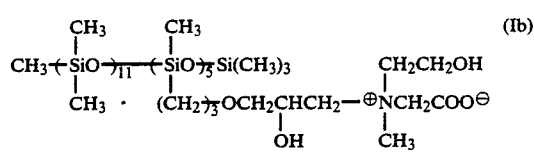
(Ib)

For surface tension measurement, a 0.1 wt % aqueous solution was prepared from the siloxane compound having average composition formula (Ib). The surface tension was 29.0 dyne/cm at 20° C.

Although some preferred embodiments have been described, many modifications and variations may be made thereto in the light of the above teachings. It is therefore to be understood that within the scope of the appended claims, the invention may be practiced otherwise than as specifically described.

We claim:

1. A betaine radical-containing siloxane compound having the following formula:

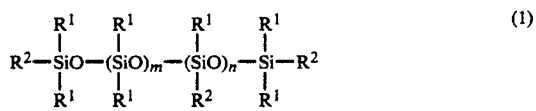
(1)

wherein $R^1$ is independently selected from substituted or unsubstituted monovalent hydrocarbon radicals having 1 to 18 carbon atoms, $R^2$ is independently selected from the group consisting of a substituted or unsubstituted monovalent hydrocarbon radical having 1 to 18 carbon atoms and a monovalent organic radical of the formula:

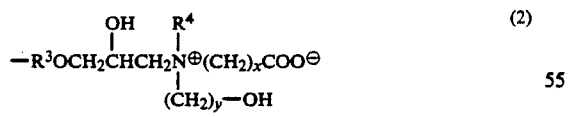
(2)

wherein $R^3$ is a divalent hydrocarbon radical having 1 to 10 carbon atoms, $R^4$ is an alkyl radical having 1 to 3 carbon atoms or $-(CH_2)_y-OH$, letters x and y are integers of from 1 to 3, with the proviso that at least one of $R^2$ substituents is of formula (2), and letters m and n are integers of from 0 to 1000.

2. The compound of claim 1 wherein $R^1$ in formula (1) is $CH_3$.

3. The compound of claim 1 which is

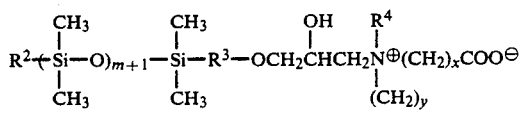

wherein $R^2$, $R^3$, $R^4$, m, x and y are as defined above.

4. The compound of claim 1 which is

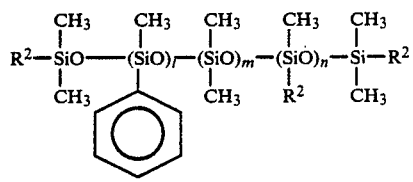

wherein $R^2$, m and n are as defined above, and l ranges from 1 to 1000.

5. The compound of claim 1 which is

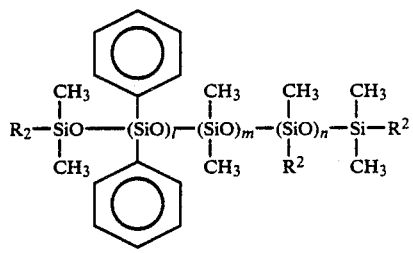

wherein $R^2$, m and n are as defined above, and l ranges from 1 to 1000.

6. The compound of claim 1 wherein in formula (2), $R^4$ is $CH_3$ and y=2.

7. The compound of claim 1 wherein in formula (2), $R^4$ is $CH_2CH_2OH$ and y=2.

8. The compound of claim 1 wherein in formula (2), x=1.

9. The compound of claim 1 wherein in formula (2), x=2.

10. A method for preparing a betaine radical-containing siloxane compound having the following formula:

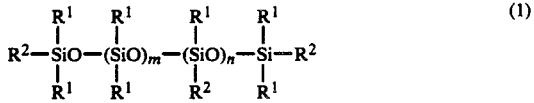
(1)

wherein $R^1$ is independently selected from substituted or unsubstituted monovalent hydrocarbon radicals having 1 to 18 carbon atoms, $R^2$ is independently selected from the group consisting of a substituted or unsubstituted monovalent hydrocarbon radical having 1 to 18 carbon atoms and a monovalent organic radical of the formula:

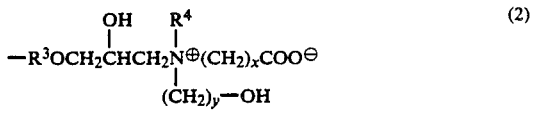
(2)

wherein $R^3$ is a divalent hydrocarbon radical having 1 to 10 carbon atoms, $R^4$ is an alkyl radical having 1 to 3 carbon atoms or $-(CH_2)_y-OH$, letters x and y are integers of from 1 to 3, with the proviso that at least one of $R^2$ substituents is of formula (2), and letters m and n are integers of from 0 to 1000, said method comprising the steps of:

reacting a compound of the formula:

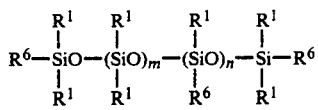 (3)

wherein $R^1$ is as defined above, $R^6$ is an organic radical independently selected from the group consisting of a substituted or unsubstituted monovalent hydrocarbon radical having 1 to 18 carbon atoms and an organic radical of the formula:

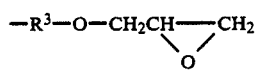 (4)

wherein $R^3$ is a divalent hydrocarbon radical having 1 to 10 carbon atoms, with the proviso that at least one of $R^6$ substituents is of formula (4), and letters m and n are as defined above, with an N-alkylaminoalcohol of the following formula:

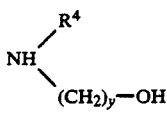 (5)

wherein $R^4$ is an alkyl radical having 1 to 3 carbon atoms, and y is as defined above, under atmospheric pressure, thereby synthesizing a compound having an organic radical of the following formula:

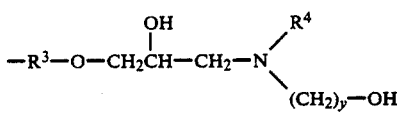 (6)

wherein $R^3$, $R^4$, and y are as defined above, and reacting said compound with a compound of the following formula:

 (7)

wherein X is a halogen atom, M is an alkali metal ion, and x is as defined above.

11. The method of claim 10 wherein the last-mentioned reaction step is carried out at a temperature of 90° to 110° C.

12. The method of claim 10 wherein the last-mentioned reaction step uses a compound of formula (7) wherein X=Cl and $M^+=Na^+$.

13. The method of claim 10 wherein the last-mentioned reaction step uses a compound of formula (7) wherein X=Cl and $M^+=K^+$.

14. The method of claim 10 wherein the last-mentioned reaction step uses isopropanol solvent.

15. The method of claim 10 wherein the last-mentioned reaction step uses propylene glycol solvent.

16. A method for preparing a betaine radical-containing siloxane compound as set forth in claim 1, comprising the step of:

reacting a compound of the formula:

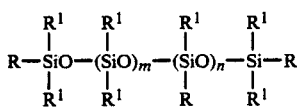

wherein R is an organic radical of the following formula:

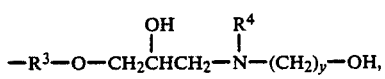 (6)

$R^1$, $R^3$, $R^4$, m, n and y are as defined above, with a compound having the following formula:

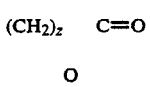

wherein z ranges from 2 to 5.

17. The method of claim 16 wherein the reaction is carried out in the presence of isopropanol solvent.

18. The method of claim 16 wherein the reaction is carried out in the presence of propylene glycol solvent.

* * * * *